(12) United States Patent
Eda (10) Patent No.: US 7,239,903 B2
(45) Date of Patent: Jul. 3, 2007

(54) BRAIN FUNCTION MEASUREMENT DEVICE, BRAIN FUNCTION MEASUREMENT METHOD, AND BRAIN FUNCTION MEASUREMENT PROGRAM

(75) Inventor: Hideo Eda, Tokyo (JP)

(73) Assignee: National Institute of Information and Communications Technology, Tokyo (JP)

(*) Notice: Subject to any disclaimer, the term of this patent is extended or adjusted under 35 U.S.C. 154(b) by 218 days.

(21) Appl. No.: 11/003,827

(22) Filed: Dec. 3, 2004

(65) Prior Publication Data

US 2005/0272988 A1    Dec. 8, 2005

(30) Foreign Application Priority Data

Jun. 7, 2004    (JP)    ............................ P2004-167903

(51) Int. Cl.
 *A61B 5/00* (2006.01)
(52) U.S. Cl. ........................................ 600/310; 600/328
(58) Field of Classification Search ................ 600/323, 600/326, 328, 473, 476, 310
See application file for complete search history.

(56) References Cited

U.S. PATENT DOCUMENTS

| 4,223,680 A | * | 9/1980 | Jobsis ......................... 600/324 |
| 5,902,235 A | * | 5/1999 | Lewis et al. ................. 600/323 |
| 6,335,792 B1 | * | 1/2002 | Tsuchiya ..................... 600/310 |
| 6,430,513 B1 | * | 8/2002 | Wang et al. ................. 600/310 |
| 6,615,065 B1 | * | 9/2003 | Barrett et al. ............... 600/323 |
| 2002/0173713 A1 | * | 11/2002 | Pfefferbaum et al. ....... 600/407 |

FOREIGN PATENT DOCUMENTS

JP    2003-339677    2/2003

* cited by examiner

*Primary Examiner*—Eric F Winakur (57) ABSTRACT

In addition to irradiating examination light toward the inside of the bead of the subject and detecting the examination light reflected from the head: structural data indicating the head structure, wherein the head is divided into multiple materials and the various materials are further divided into multiple elements, are stored in a structural data storage unit set up in a specified region of memory; the optical properties of the aforementioned elements are calculated from a given specified initial value; the hemodynamics inside the brain of the subject are calculated based on the optical properties thereof, and the aforementioned initial values are taken to be the optical properties when the light intensity signal values, provisionally calculated from optical properties under the assumption that the optical properties are uniform for each of the aforementioned materials, are in a fixed range of the actually measured light intensity signal values.

11 Claims, 9 Drawing Sheets

STRUCTURAL DATA

| Element No. | Coordinates | Material |
|---|---|---|
| 1 | (1,0,0) | White Matter |
| 2 | (2,0,0) | White Matter |
| 2367 | (5,4,16) | Gray Matter |
| 6958 | (6,3,5) | CSF |
| 25869 | (7,3,5) | Bone |
| 69584 | (15,12,19) | Scalp |

Element Data ↗ (rows 1, 2)
Element Data ↗ (row 6958)

FIG.6

OPTICAL PROPERTIES DATA

| Element No. 1 | | |
|---|---|---|
| Time | Absorption Coefficient | Reduced Scattering Coefficient |
| t1 | 0.025 | 1.8 |
| t2 | 0.026 | 1.5 |
| ... | ... | ... |
| tn | 0.036 | 1.9 |

| Element No. 2 | | |
|---|---|---|
| Time | Absorption Coefficient | Reduced Scattering Coefficient |
| t1 | 0.035 | 0.58 |
| t2 | 0.056 | 0.59 |
| ... | ... | ... |
| tn | 0.039 | 0.60 |

BRAIN FUNCTION MEASUREMENT DEVICE, BRAIN FUNCTION MEASUREMENT METHOD, AND BRAIN FUNCTION MEASUREMENT PROGRAM

FIELD OF THE INVENTION

The present invention relates to brain function measurement device and a brain function measurement program that calculates the hemodynamics of the brain and measures brain function by irradiating examination light such as near infrared light on the head of the subject, and measuring the intensity of the light that passes through or is scattered from the brain.

DESCRIPTION OF RELATED ART

In recent years, progress has been made in developing brain measurement devices that utilize light, specifically, near infrared light, and that can measure the brain function of a subject when not restrained.

In this type of device, as described in Japanese Unexamined Patent Application Publication No. 2003-39677, optical properties (absorption coefficient, and reduced scattering coefficient) are calculated at various areas in the brain by irradiating the head of the subject and measuring the absorbance of near infrared light of specified multiple wavelengths that pass through or are scattered out of the inside of the brain. The hemodynamics indicating the activity of the brain can be calculated therefrom. The aforementioned optical properties are closely related to changes in the amounts or changes in the concentrations of oxygenated hemoglobin (oxyHb), deoxygenated hemoglobin (deoxyHb), and total hemoglobin (totalHb), which are biological substances that participate in the hemodynamics of the brain. These hemoglobin parameters (oxyHb, deoxyHb and totalHb) are calculated from absorption coefficients. An indirect understanding of the activity of the brain may be obtained from these optical properties. In the past, the head was considered a semi-infinite, uniform body, and the optical properties at various areas in the brain were calculated by fitting the measured values of the aforementioned light to a uniform model solution of an optical diffusion equation.

SUMMERY OF THE INVENTION

Nonetheless, the head has a complex structure comprising various types of materials such as the scalp, skull, CSF, and brain (white matter, gray matter). Because the head cannot be called a uniform physical body, whether or not the optical properties derived in the past could reflect the actual optical properties of the brain and the hemodynamics based thereon was extremely dubious.

Thus, the present inventors set up a head structure model comprising the aforementioned materials, divided these materials into multiple (tens to hundreds of thousands of) elements by detailed segmentation, and attempted to calculate the optical properties of the various elements from measured values. This approach had iterative calculations of the forward and inverse problem. In order to obtain a solution, an optimization method was employed in which initial values for optical properties were set for the various elements, the intensity of the light calculated therefrom was compared to the intensity of the light actually measured, and the optical properties of the various elements were successively varied so that the difference became smaller.

In this regard, because of the very fact that it is difficult to derive the optical properties relating to many elements from dozens of optical measurement values, the method of setting the initial value in this way did not provide a solution, and completely meaningless results were output.

In contrast, even though optimal initial values must be set, for example, by using reference values, etc., subjects have individual differences, and a solution is not necessarily obtained.

Moreover, in order to confirm whether or not the initial values were correctly set, the solutions relating to many elements must be calculated and the analytic results awaited. In this regard, an enormous amount of time is required before the results are output, and if unsuitable analytic results appear, then initial values must be reset and the calculations reworked, leading to a great amount of wasted time and money.

Thus, the present invention is a kind of brain function measurement device in which a close-to-actual head structure model is used to enable precise measurement of the optical properties of the brain of the subject and the hemodynamics based thereon. The primary issue addressed was to be able to optimally set the initial values related to the optical properties calculation of the various elements, which is one of the problems at this time.

Specifically, the brain function measurement device related to the present invention uses a light irradiation means that irradiates examination light toward the inside of the head of the subject, and a light receiving means that receives the examination light exiting from the head and outputs light intensity signals indicating the light intensity thereof, and is characterized by comprising the following structural elements (1) to (3).

(1) A structural data storage unit that stores structural data indicating the head structure wherein the head is divided into multiple materials, and the various materials are further divided into multiple elements;

(2) A calculator that calculates optical properties of the aforementioned elements from a given specified initial value, and calculates the hemodynamics inside the brain of the subject based on the optical properties thereof; and (3) An initial values calculator that provisionally stipulates the optical properties of the various materials under the assumption that the optical properties are uniform for each material, and takes the aforementioned initial values to be the provisional optical properties when the light intensity signal values calculated from these provisional optical properties are in a fixed range of the actually measured light intensity signal values.

With this kind of device, the optical properties of the brain, which in the past were derived by a uniform model, are derived based on a head structure model divided into materials that is closer to the actual head structure, and therefore optical properties of the brain and hemodynamics based thereon can be calculated in a manner vastly more accurate than in the past.

In addition, the initial values of the various elements, which are one of the major problems at this time, can be calculated objectively and automatically based on the aforementioned head structure model, and therefore, the disadvantages of analytic results based on having set inappropriate initial values can be reduced. Moreover, these initial values include unknown quantities (absorption coefficients and reduced scattering coefficients) only two times the number of targeted brain structures (materials), and initial values can be calculated in a short time by obtaining light intensity signals at only several dozen places without mathematically ill-conditions problem.

More concretely, it is preferable for the aforementioned initial values calculator to calculate the aforementioned initial values by making successive updates using specified values input as a point of departure such that the light intensity signal values, calculated based on the aforementioned provisional optical properties, approach the measured light intensity signal values.

Dividing the head into the five materials of the scalp, skull, CSF, gray matter and white matter may be cited as a specific embodiment of the aforementioned structural data.

The calculations become complex, but to enable precise calculations by matching the individual differences between subjects, the aforementioned structural data may be obtained by making actual measurements of the head of the subject. MRI and CT may be used for the actual measurements.

To obtain rapid analytic results by simplifying the calculations, the aforementioned structural data may be common data obtained from a general model.

On a practical level, it is preferable to use near infrared light of stipulated multiple wavelengths as the aforementioned examination light.

In addition, the present invention is also a brain function measurement method characterized in that the following steps (1) through (5) are provided.

(1) Irradiating light using a light irradiation means to irradiate examination light toward the inside of the head of the subject;

(2) Receiving light using a light receiving means to receive examination light exiting from the head, and to output light intensity signals that indicate the light intensity thereof;

(3) Storing structural data via storage in a structural data storage unit set up in a specified region of memory structural data indicating the head structure wherein the head is divided into multiple materials, and then the various materials are further divided into multiple elements;

(4) Calculating the optical properties of the various aforementioned elements from given specified initial values, and calculating the hemodynamics in the brain of the subject based on the optical properties thereof; and (5) Calculating initial values by taking the aforementioned initial values to be the various optical properties when the light intensity values calculated from optical properties, provisionally stipulated under the assumption that the optical properties are uniform for each material, are in a fixed range of the actually measured light intensity signal values.

In addition, the present invention is a brain function measurement program, which uses a light irradiation means that irradiate examination light toward the inside of the head of the subject, and a light receiving means that receives the examination light exiting from the head and outputs light intensity signals indicating the light intensity thereof, characterized in that a computer manifests the functions of the following units (1) through (3):

(1) A structural data storage unit that stores structural data indicating the head structure wherein the head is divided into multiple materials, and the various materials are further divided into multiple elements, (2) A calculator that calculates optical properties of the aforementioned elements from given specified initial values, and calculates the hemodynamics inside the brain of the subject based on the optical properties thereof; and (3) An initial values calculator that provisionally stipulates the optical properties of the various materials under the assumption that the optical properties are uniform for each material, and that takes the aforementioned initial values to be the provisional optical properties when the light intensity signal values calculated from these provisional optical properties are in a fixed range of the actually measured light intensity signal values.

According to the present invention configured in this way, the optical properties of the brain, which in the past were derived by a uniform model, are derived based on a bead structure model closer to the actual head structure, and therefore optical properties of the brain and hemodynamics based thereon can be calculated in a manner vastly more accurate than in the past.

In addition, the initial values of the various elements, which are one of the major problems at this time, can be calculated objectively and automatically based on the aforementioned bead structure model, and therefore, the disadvantages of analytic results based on having set inappropriate initial values can be reduced. Moreover, these initial values include unknown quantities (absorption coefficients and reduced scattering coefficients) only two times the number of targeted brain structures (materials), and initial values can be calculated in a short time by obtaining light intensity signals at only several dozen places without mathematically ill-conditions problem.

DETAILED DESCRIPTION OF THE PREFERRED EMBODIMENTS

An embodiment of the brain function measurement system of the present invention will be explained while referring to diagrams.

Figure 1:
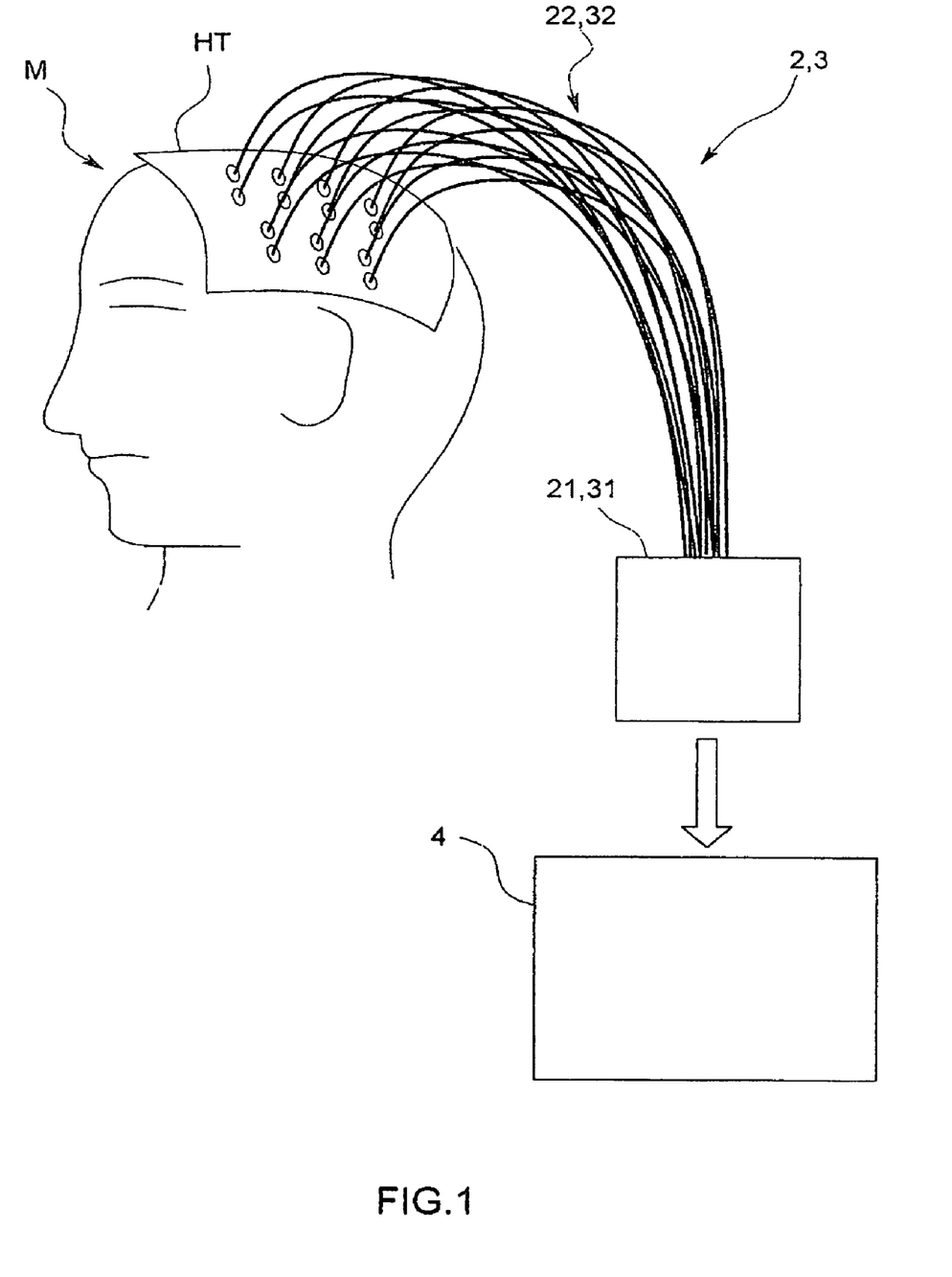
FIG. 1 is a schematic overall configuration diagram indicating a brain function measurement system of one embodiment of the present invention.
Figure 2:
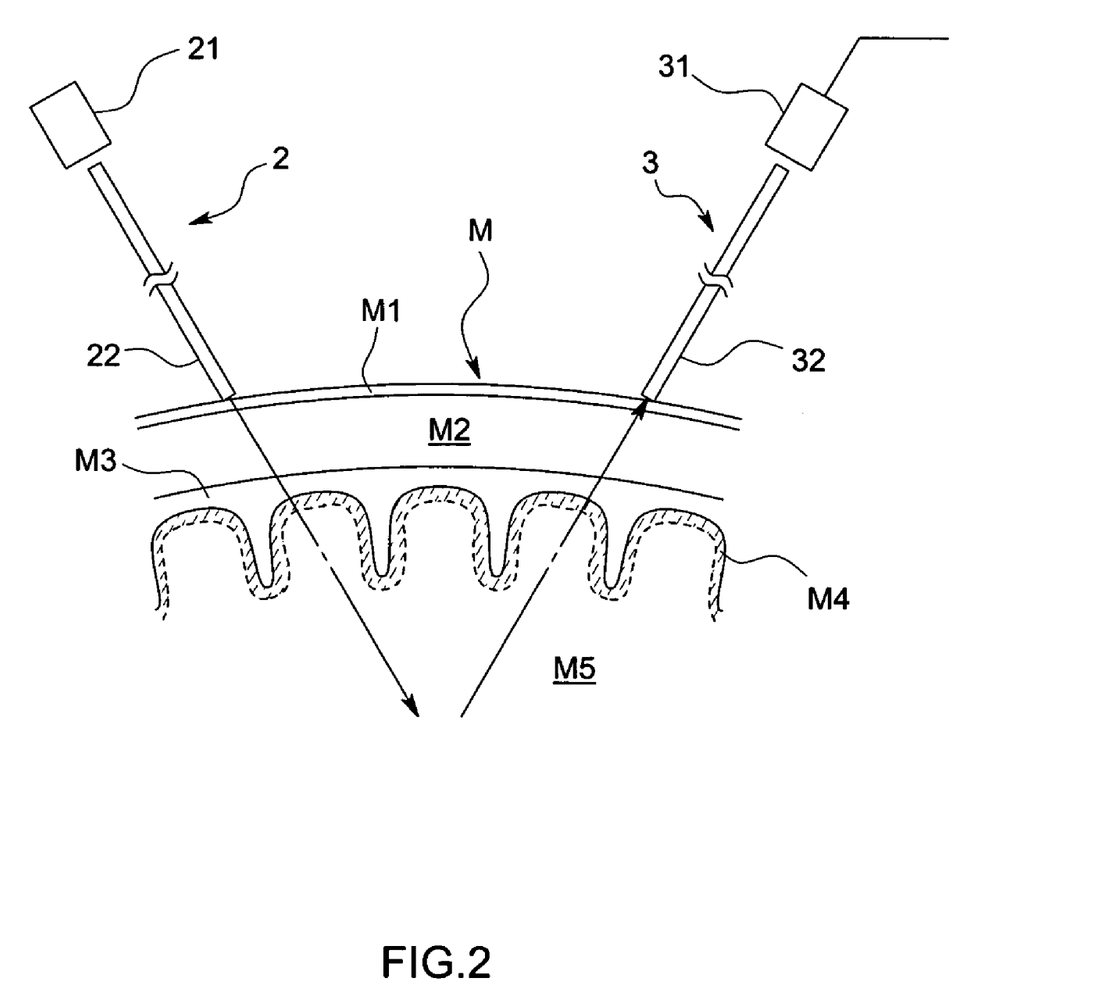
FIG. 2 is a schematic diagram indicating the state of irradiating the inside of the head with near infrared light according to the same embodiment.

This brain function measurement system utilizing NIRS (near infrared spectroscopy), and as indicated in FIGS. 1 and 2, compromises: a light irradiation means or unit 2 that irradiates examination light toward the inside of the head of the subject; a light receiving means or unit 3 that receives the examination light exiting from the head, and outputs light intensity signals indicating the light intensity thereof and a brain function measurement device 4 that calculates the hemodynamics of the brain of the subject by receiving the aforementioned light intensity signals.

The various parts will be explained.

As indicated in FIGS. 1 and 2, the light irradiation means 2 comprises a light source 21 such as a semiconductor laser that emits near infrared light of multiple wavelengths (3 wavelengths in the present embodiment), and flexible light guides (optical fibers) 22 for transmitting light emitted from a light source 21. The outgoing light guide end part of this light guide 22 for transmitting light is held in a helmet-like head-mounted tool HT. When mounted on the subject, the aforementioned head-mounted tool HT is configured such that near infrared light are irradiating toward the inside of the head M of the subject.

As indicated in FIGS. 1 and 2, the light receiving means 3 comprises flexible incoming light guides (optical fibers) 32 for receiving light with the light guide end parts held in the aforementioned head-mounted tool HT, a light receiving element 31 such as a photo multiplier tube or a CCD element connected to the light conducting end parts of these light guides 32 for receiving light, and an amplifier not indicated in the diagrams. The light receiving means 3 is configured such that the near infrared light irradiated from the aforementioned light guide 22 for transmitting light and reflected by or passing through the inside of the head M of the subject are guided to the light receiving element 31 through the aforementioned light guides 32 for receiving light, and are output as light intensity signals that are electric signals indicating the light intensity thereof. The light guides 22 for transmitting light and the light guides 32 for receiving light are paired, and in this embodiment, multiple mutually separated pairs thereof are held in the head-mounted tool HT.

Figure 3:
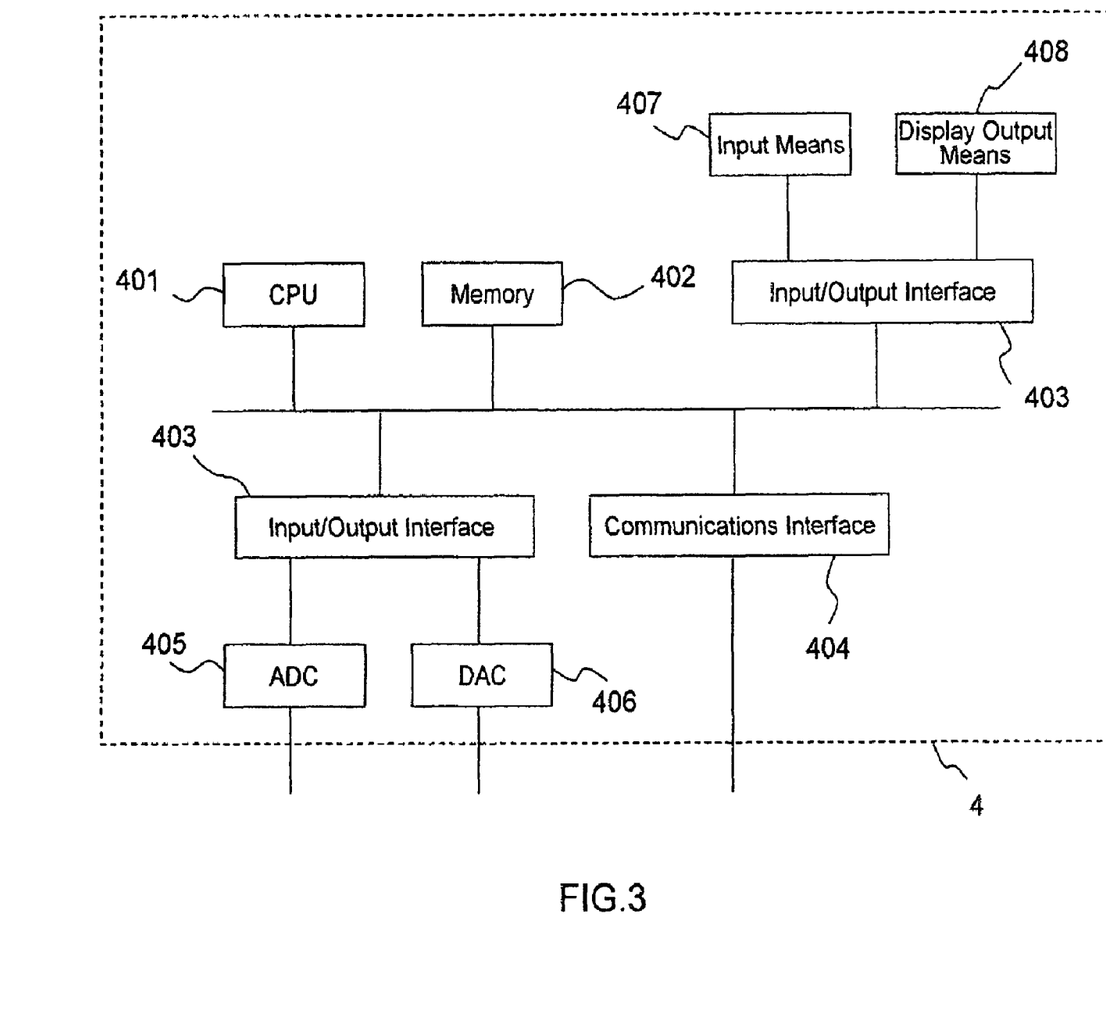
FIG. 3 is a hardware configuration diagram of a brain function measurement device of the same embodiment.
Figure 4:
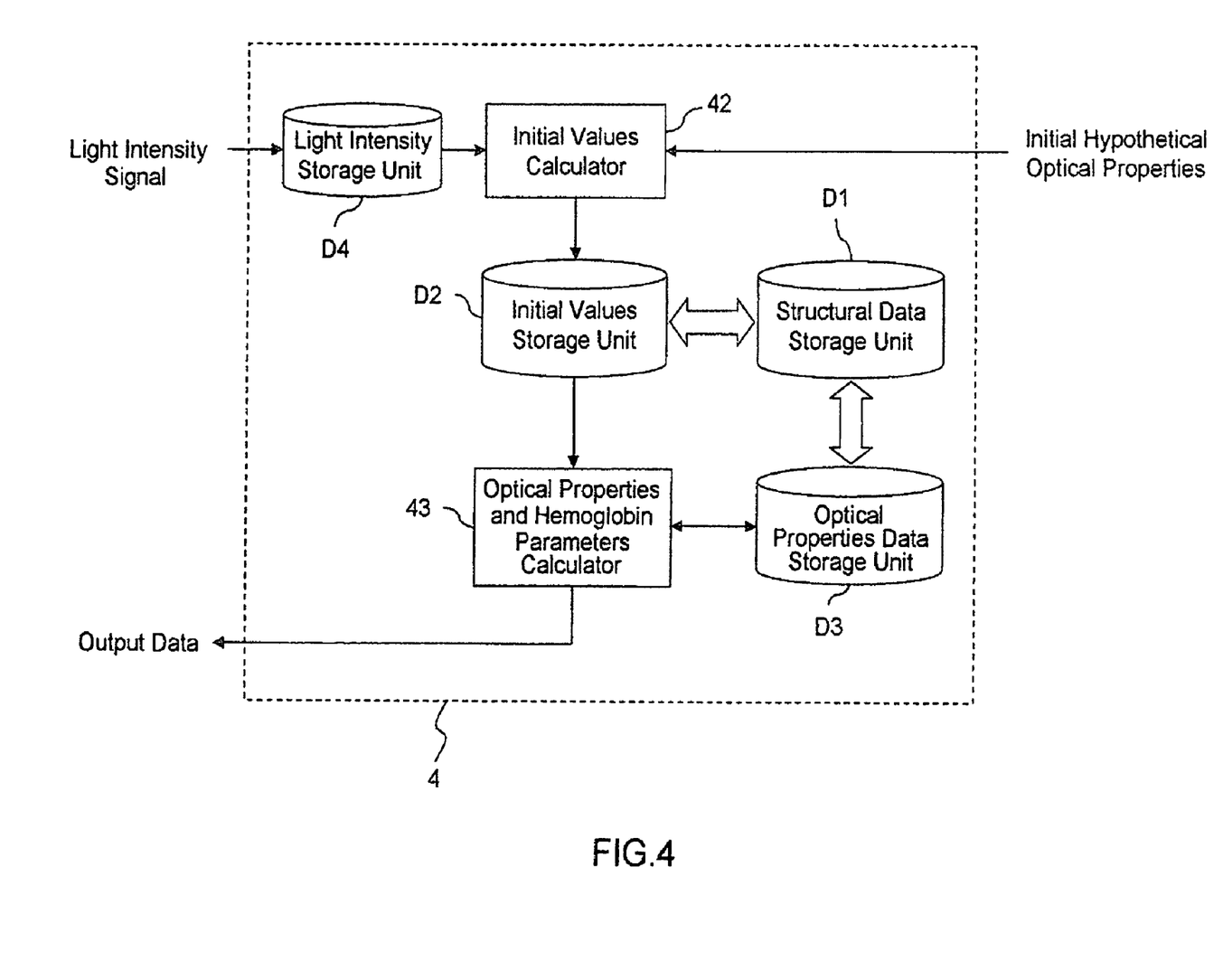
FIG. 4 is a function block diagram of a brain function measurement device of the same embodiment.

As indicated in FIGS. 3 and 4, the brain function measurement device 4 is a computer system comprising a CPU 401, a non-volatile or volatile memory 402, an AD converter 405, a DA converter 406, an input/output interface 403, display output means 408 such as a display, input means 407 such as a keyboard or mouse, and a communications interface 404. Such functions as a structural data storage unit D1 to be described later, an optical properties and hemoglobin parameters calculator 43, and an initial values calculator 42 are manifested by joint operation of peripheral equipment, especially the aforementioned CPU 401, following a specified program memorized in the aforementioned memory 402. The brain function measurement device 4 in question may comprise a single unit or multiple computers. Of course, the brain function measurement device 4 may be comprised by using a general purpose computer and by programming software into memory, but may also be comprised completely or partially by hardware using custom logic circuits.

Figure 5:
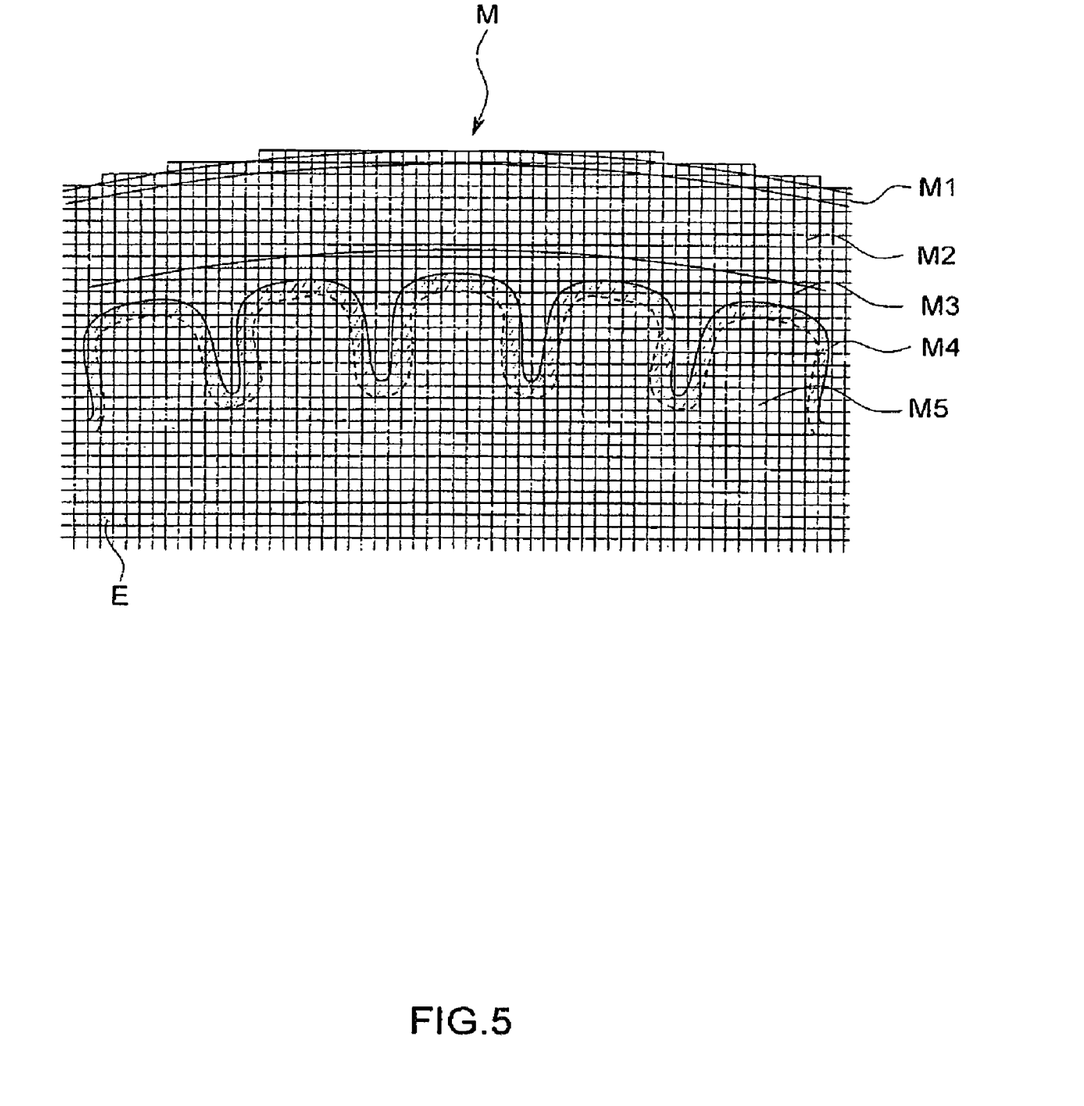
FIG. 5 is a schematic diagram indicating a two-dimensional model of a head structure of the same embodiment.
Figure 6:
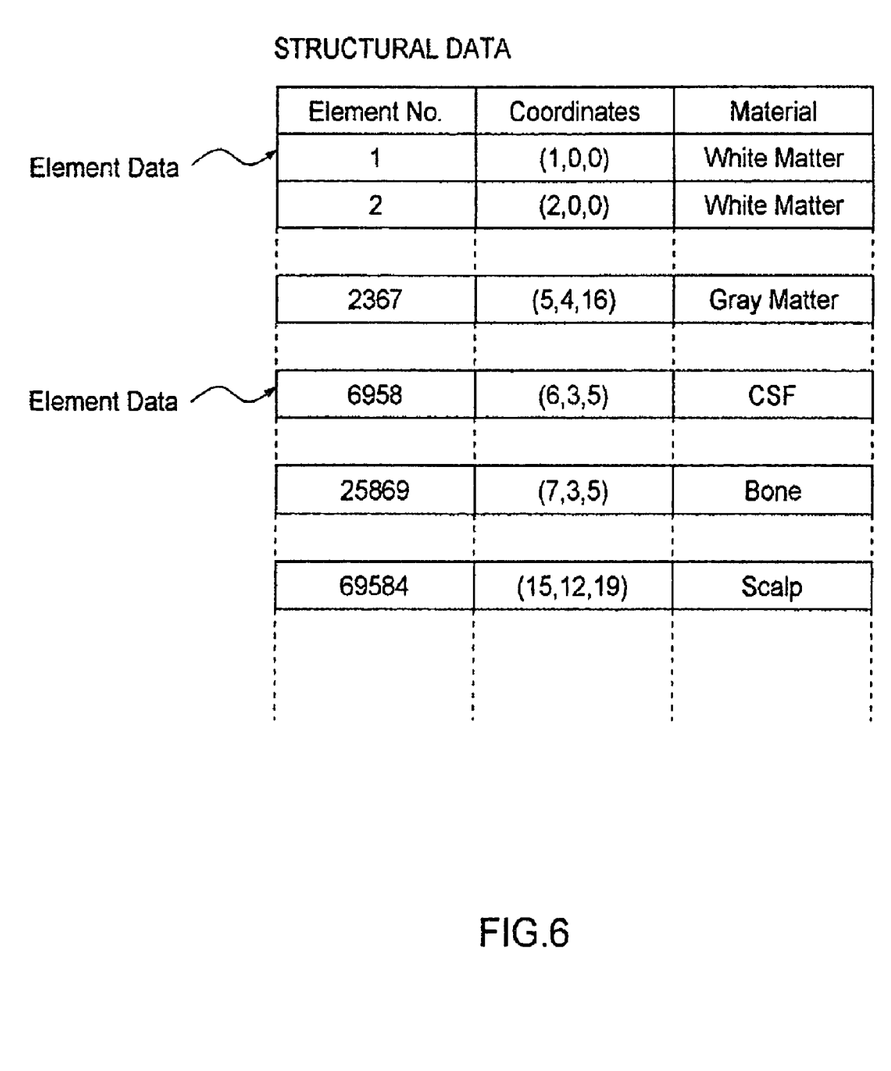
FIG. 6 is a schematic internal structure diagram indicating the structural data storage unit of the same embodiment.

The structural data storage unit D1 is set up in a specified region of the aforementioned memory 402, and stores structural data indicating the head structure (refer to FIG. 5, however, the head structure in this diagram is two dimensional whereas the actual head structure is three dimensional) wherein the head M is divided into multiple materials M1 to M5, and the materials M1 to M5 are further divided into multiple elements E (many, tens to hundreds of thousands). Specifically, as indicated in FIG. 6, this structural data comprises element data indicating various elements, and the contents of the various elements comprise at least the coordinates and materials of these elements. Here, as indicated in FIG. 2 and FIG. 5, the five classifications of materials are the scalp M1, skull M2, cerebrospinal fluid M3, gray matter M4, and white matter M5. In order to enable precise measurements matching individual subject differences, the structural data in question is most preferably created from measured values of the head M of the subject using MRI or CT. Here, in order to obtain high-speed analytic results by simplifying the calculations, a standard obtained from a general model was set up.

The optical properties and hemoglobin parameters calculator 43 calculates the optical properties of the aforementioned elements from the given specified initial values, creates time series data of optical properties for each element from the optical properties at multiple sampling times, and calculates the hemoglobin parameters in the brain of the subject based on these time series data. To calculate the optical properties, suitable initial values are set for the optical properties related to the various elements, the light intensity signal values of the near infrared light actually received and measured are compared with the light intensity signal values of the near infrared lights calculated iteratively from these initial values, and an optimization method is used by successively varying the optical properties of the elements such that this difference becomes smaller. Then, the optical properties of the elements when the calculated values of the light intensity signals are finally in a fixed range of the actual values are taken to be the results of the calculations, and are stored in an optical properties data storage unit D3 set up in a specified region of memory.

Figure 7:
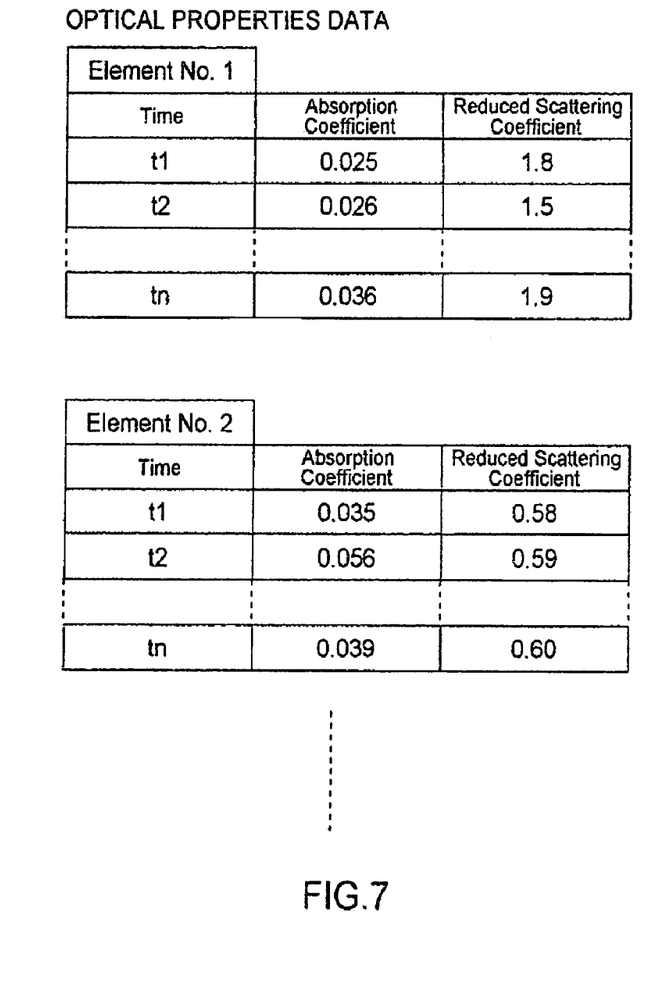
FIG. 7 is a schematic internal structure diagram indicating the optical properties data storage unit of the same embodiment.

The aforementioned optical properties of the various elements are stored in the optical properties data storage unit D3 in a time series, and the optical properties data, which is the time series data of the optical properties, are stored as indicated in FIG. 7. This optical properties data is related to the aforementioned element data, and the optical properties comprise at a minimum the absorption coefficients and the reduced scattering coefficients of the various elements.

Further, because the configuration of calculating the hemoglobin parameters in the brain from optical properties data calculated in this way, and outputting to a display, etc. is already well known, a detailed explanation will be omitted.

The initial values calculator 42 calculates the initial values of the elements using the aforementioned optical properties and hemoglobin parameters calculator 43, and is a part that characterizes the present embodiment.

The initial values calculator 42 provisionally stipulates the optical properties of the various materials under the assumption that the optical properties are uniform for each material, and when the light intensity signal values calculated from these provisional optical properties are in a fixed range of the measured light intensity signal values, these provisional optical properties signals are taken as the aforementioned initial values.

Specifically, using the optical properties (absorption coefficient and reduced scattering coefficient) of each material suitably input, for example, by an operator under the assumption that the elements comprising the same material always have the same optical properties, the light intensity signal values of the near infrared light calculated from the provisional optical properties related to the various elements are compared with the light intensity signal values of the near infrared light actually received and calculated, and similar optimization methods as previously described are used wherein the optical properties of the various elements are successively updated in order to decrease the difference thereof. Then, the initial values are taken to be the optical properties of the various elements when the calculated values of the light intensity signals finally approximate the measured values above a fixed level, and are related to the aforementioned element data and stored in an initial values storage unit D2 set up in a specified location of the memory 402.

Figure 8:
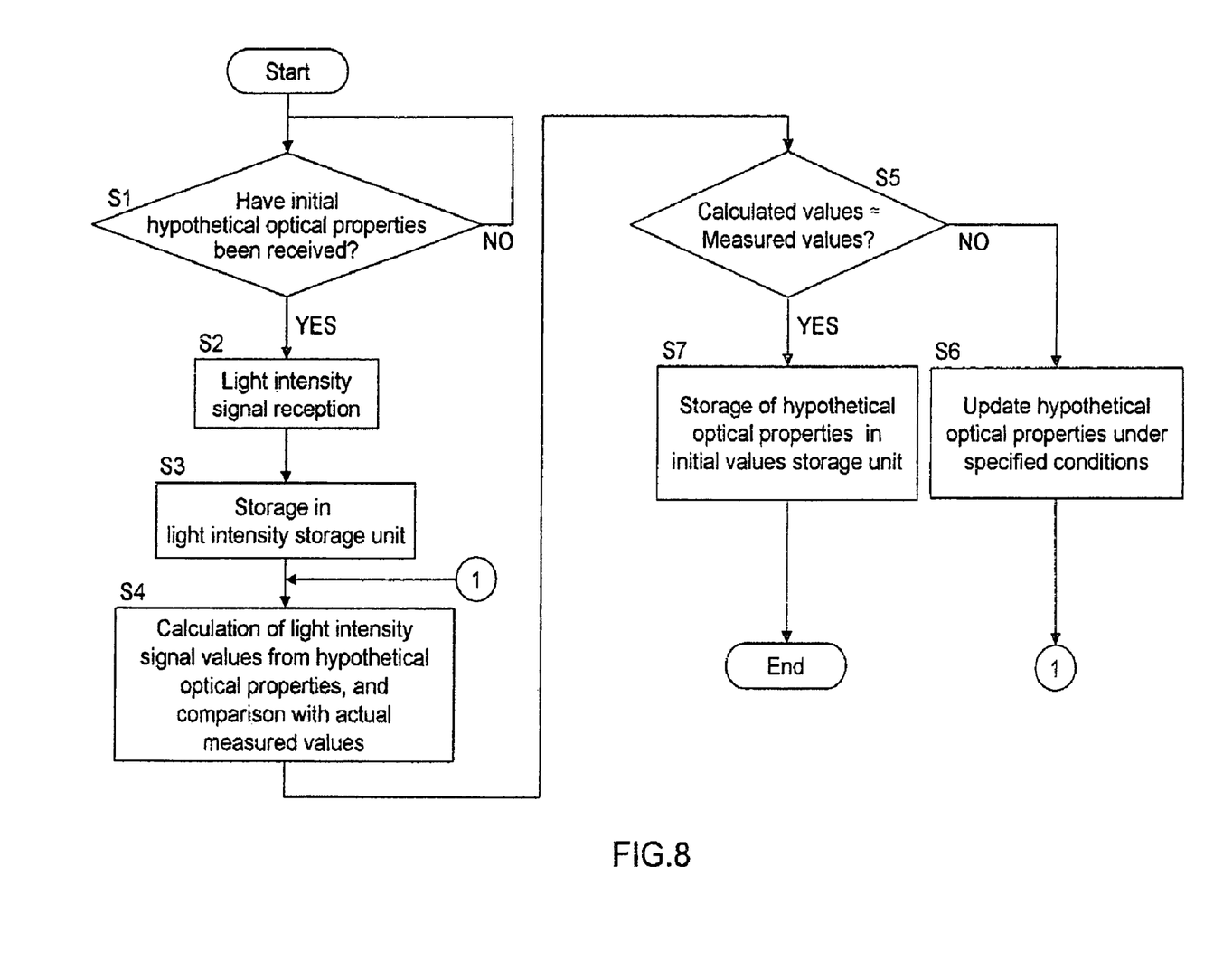
FIG. 8 is a flowchart indicating the operation of the brain function measurement device of the same embodiment.
Figure 9:
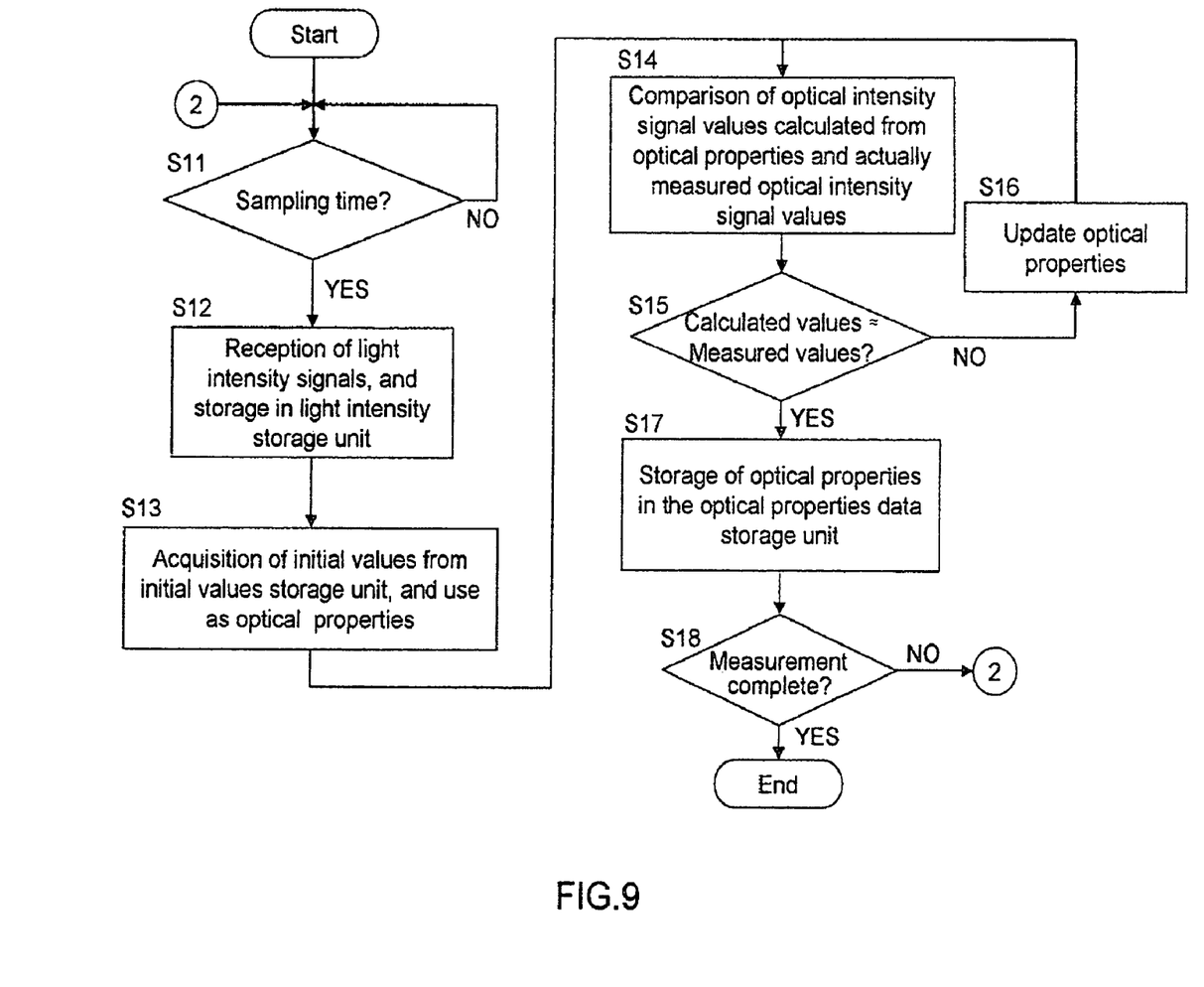
FIG. 9 is a flowchart indicating the operation of the brain function measurement device of the same embodiment.

One example of the operation of a brain function measurement system related to the present embodiment configured in this way will be explained below by referring to FIGS. 8 and 9.

First, initial provisional optical properties for each material, which are sent through the aforementioned input means 407 from an operator or through the communications interface 404 from another computer not indicated in the diagram, are received (Step S1), and these values are stored in a specified region of the memory 402. Here, five kinds of materials have been set up, each with a light absorption coefficient and an equivalent scattering coefficient, and thus ten initial provisional optical properties are memorized and stored.

Meanwhile, near infrared light are irradiated from the light irradiation means 2, and those near infrared light that pass through the head M of the subject are received by the light receiving means 3.

Then, when the specified event is generated, the light intensity signals at the various sites at that time are received (Step S2), and those values are stored in the light intensity storage unit D4 set up in a specified region in the memory 402 (Step S3).

Next, under the specified assumption that the elements comprising the same material always have the same optical properties, the aforementioned initial provisional optical properties are taken as the point of departure; the light intensity signal values of the near infrared light calculated from the provisional optical properties related to the various elements are compared with the light intensity signal values of the near infrared light actually received and calculated; and the optical properties of the various elements are successively updated in order to decrease the difference thereof (Steps S4 to S6).

Then, when the calculated values of the light intensity signals are finally in a fixed range of the measured values, the optical properties of the various elements are stored in an initial values storage unit set up in a specified location of memory as the initial values (Step S7).

The actual measurements of brain function are begun thereafter.

First, when a specified sampling time arrives (Step S11), the light intensity signals at the various sites at that time are received, and those values are stored in the aforementioned light intensity storage unit D4.

Next, the initial values for calculating the optical properties are obtained from the aforementioned initial values storage unit D2; and taking these values as the point of departure, the light intensity signal values of the near infrared light calculated from these values are compared with the light intensity signal values of the near infrared light actually received and calculated, and the optical properties of the various elements are successively updated such that the difference thereof becomes smaller (Steps S13 to S16). Then, when the calculated values of the light intensity signals are finally in a fixed range of the measured values, the optical properties of the various elements are taken as the calculated results and stored in the optical properties data storage unit D3 (Step S17).

The optical properties at the various sampling times are successively calculated in this way and are stored each time in the optical properties data storage unit D3, and time series data relating to the optical properties of the various elements are generated over a certain amount of time (Step S18).

Hemoglobin parameters, the amounts or changes in the concentrations of oxyHb, deoxyHb, and totalHb, which are biological substances that participate in the hemodynamics of the brain, are calculated from these time series data relating to the optical properties of the various elements, and the analytic results thereof are output to the display, etc. The details of this point are already well known, and will be omitted.

Consequently, according to the brain function measurement device or brain function measurement method related to the present invention configured in this way, the optical property values of the brain are derived based on a head structure model divided into materials that is closer to the actual head structure, and therefore optical property values of the brain and hemoglobin parameters based thereon can be calculated in a manner vastly more accurate than in the past.

In addition, the initial values of the optical properties of the various elements, which are one of the major problems at this time, can be objectively and automatically calculated based on the aforementioned head structure model, and therefore, the disadvantages of analytic results based on having set inappropriate initial values can be reduced. Moreover, these initial values include unknown quantities (absorption coefficients and reduced scattering coefficients) only two times the number of targeted brain structures (materials), and initial values can be calculated in a short time by obtaining light intensity signals at only several dozen places without ill-conditions problem.

Further, the present invention is not limited to the aforementioned embodiment. For example, the number of material types is not limited to five, and various transformations of the method of element generation (method of segmentation), etc. are also possible. Obviously, the flowchart can also be changed.

The invention claimed is:

1. A brain function measurement device, which uses a light irradiation unit that irradiates examination light toward the inside of a head of a subject, and a light receiving unit that receives the examination light exiting from the head and outputs light intensity signals indicating a light intensity thereof comprising:
    a structural data storage unit that stores structural data indicating a head structure wherein the head is divided into multiple materials, and the various materials are further divided into multiple elements;
    an optical properties and hemoglobin parameters calculator that calculates optical properties of the aforementioned elements from predetermined initial values that differs between the various materials, and calculates the hemoglobin parameters inside the brain of the subject based on the optical property values thereof; and
    an initial values calculator that calculates the aforementioned initial values,
    characterized in that the initial values calculator thereof provisionally stipulates the optical property values of the various materials under the assumption that the optical properties are uniform for each material, and takes the aforementioned initial values to be the accepted optical properties when the light intensity signal values calculated from these provisional optical properties are in a fixed range of the actually measured light intensity signal values.

2. A brain function measurement device according to claim 1 in which the aforementioned initial values calculator successively updates the aforementioned accepted optical properties by taking the predetermined initial values input into the initial values calculator as a point of departure such that the light intensity signal values calculated based on these predetermined initial values approach the aforementioned actually measured light intensity signal values.

3. A brain function measurement device according to claim 1 in which the aforementioned structural data classifies the head into five materials of a scalp, skull, CSF, gray matter, and white matter.

4. A brain function measurement device according to claim 1 in which the aforementioned structural data is obtained by actual measurements of the head of the subject.

5. A brain function measurement device according to claim 1 in which the aforementioned structural data is taken to be what is commonly obtained from a general model.

6. A brain function measurement device according to claim 1 in which the aforementioned examination light is near infrared light of specified multiple wavelengths.

7. A brain function measurement method comprising the steps of:
   irradiating light using light irradiation means to irradiate examination light toward an inside of a head of a subject;
   receiving light using light receiving means to receive examination light exiting from the head, and to output light intensity signals that indicate a light intensity thereof;
   storing structural data via storage in a structural data storage unit set up in a specified region of memory, the structural data indicating a head structure wherein the head is divided into multiple materials, and then the various materials are further divided into multiple elements;
   calculating the optical properties of the various aforementioned elements from predetermined initial values that differ between the various materials, and calculating the hemoglobin parameters in a brain of the subject based on the optical properties thereof; and
   calculating initial values by taking the predetermined initial values to be the accepted optical properties when the optical intensities calculated from the optical properties, provisionally stipulated under the assumption that the optical properties are uniform for each material, are in a fixed range of the actually measured light intensity signal values.

8. A brain function measurement method according to claim 7 wherein the aforementioned initial values calculation step is conducted such that the light intensity signal values calculated based on the aforementioned accepted optical properties approach the actually measured light intensity signal values, and such that the predetermined initial values are re-calculated by successively updating the predetermined values input as a point of departure.

9. A computer readable storage medium storing a brain function measurement program, which is executable on a computer that uses a light irradiation unit that irradiates examination light toward the inside of the head of the subject, and a light receiving unit that receives the examination light exiting from the head and outputs light intensity signals indicating the light intensity thereof, characterized in that a computer executing the proaram performs the functions of:
   a structural data storage unit that stores structural data indicating the head structure wherein the head is divided into multiple materials, and the various materials are further divided into multiple elements;
   an optical properties and hemoglobin parameters calculator that calculates optical properties of the aforementioned elements from predetermined initial values that differ between the various materials, and calculates the hemoglobin parameters inside the brain of the subject based on the optical properties thereof; and
   an initial values calculator that provisionally stipulates the optical properties of the various materials under the assumption that the optical properties are uniform for each material, and that takes the aforementioned initial values to be the accepted optical properties when the light intensity signal values calculated from these provisional optical properties are in a fixed range of the actually measured light intensity signal values.

10. A brain function measurement program according to claim 9 in which the aforementioned initial values calculator successively updates the aforementioned accepted optical properties by taking predetermined values input into the initial values calculator as a point of departure such that the light intensity signal values calculated, based on these values, approach the aforementioned actually measured light intensity signal values.

11. A brain function measurement device for measuring functional activity of an in vivo brain, comprising:
   a light irradiation unit for irradiating selective positions of the brain by directing light of predetermined wavelengths into a head of a living subject;
   a light receiving unit for detecting the light of predetermined wavelengths of the light irradiation unit after interaction with the head of the living subject and providing light detection signals;
   a structural data storage unit storing a predetermined set of structural data representative of a head of a type of the living subject including a plurality of data elements for each of a scalp, a bone, a brain white matter, a brain gray matter and cerebrospinal fluid, the data for each of the plurality of data elements includes an absorption coefficient and a reduced scattering coefficient that differ between the various materials; and
   a computer system for
      (a) receiving the light detection signals from the light receiving unit and coordinating each light detection signal with the data elements and storing the coordinated light detection signals in a light intensity storage unit,
      (b) processing the light detection signals with the predetermined set of structural data for each of the plurality of data elements to determine the hemoglobin parameters of the living subject brain,
      (c) one of (i) modifying the predetermined set of structural data in the structural data storage unit when the hemoglobin parameters are beyond a predetermined range, and (ii) outputting the hemoglobin parameters when the hemoglobin parameters are within the predetermined range, and
      (d) repeating the irradiation, detection and processing of the light detection signals until the hemoglobin parameters of the living subject brain are within the predetermined range.

* * * * *